United States Patent
Forrow et al.

(10) Patent No.: US 8,163,160 B2
(45) Date of Patent: *Apr. 24, 2012

(54) BIOSENSOR HAVING IMPROVED HEMATOCRIT AND OXYGEN BIASES

(75) Inventors: Nigel J. Forrow, Abingdon (GB); Shridhara Alva Karinka, Pleasanton, CA (US)

(73) Assignee: Abbott Diabetes Care Inc., Alameda, CA (US)

( * ) Notice: Subject to any disclaimer, the term of this patent is extended or adjusted under 35 U.S.C. 154(b) by 14 days.

This patent is subject to a terminal disclaimer.

(21) Appl. No.: 12/815,169

(22) Filed: Jun. 14, 2010

(65) Prior Publication Data

US 2011/0031133 A1 Feb. 10, 2011

Related U.S. Application Data

(63) Continuation of application No. 11/420,628, filed on May 26, 2006, now Pat. No. 7,754,093, which is a continuation-in-part of application No. 10/278,657, filed on Oct. 23, 2002, now Pat. No. 7,501,053.

(51) Int. Cl.
G01N 27/327 (2006.01)
G01N 33/50 (2006.01)
G01F 1/64 (2006.01)

(52) U.S. Cl. ............... 205/777.5; 205/792; 204/403.01; 204/403.02; 204/403.04; 204/403.14; 252/62.2; 252/500

(58) Field of Classification Search ............... 205/792, 205/777.5; 204/403.01, 403.02, 403.04, 204/403.14; 435/287.1, 287.3, 287.9, 817
See application file for complete search history.

(56) References Cited

U.S. PATENT DOCUMENTS

| | | | |
|---|---|---|---|
| 5,147,806 A | 9/1992 | Kamin et al. | |
| 5,262,305 A | 11/1993 | Heller | |
| 5,264,104 A | 11/1993 | Gregg et al. | |
| 5,320,725 A | 6/1994 | Gregg et al. | |
| 5,356,786 A | 10/1994 | Heller et al. | |
| 5,593,852 A | 1/1997 | Heller et al. | |
| 5,665,222 A | 9/1997 | Heller et al. | |
| 5,708,247 A | 1/1998 | McAleer et al. | |
| 5,951,836 A | 9/1999 | McAleer et al. | |
| 5,972,199 A | 10/1999 | Heller et al. | |
| 6,103,033 A | 8/2000 | Say et al. | |
| 6,120,676 A | 9/2000 | Heller et al. | |
| 6,134,461 A | 10/2000 | Say et al. | |
| 6,143,164 A | 11/2000 | Heller et al. | |
| 6,175,752 B1 | 1/2001 | Say et al. | |
| 6,271,045 B1 | 8/2001 | Douglas et al. | |
| 6,284,125 B1 | 9/2001 | Hodges et al. | |
| 6,287,451 B1 | 9/2001 | Winarta et al. | |
| 6,338,790 B1 | 1/2002 | Feldman et al. | |
| 6,746,582 B2 | 6/2004 | Heller et al. | |
| 7,501,053 B2 * | 3/2009 | Karinka et al. | ............... 205/792 |
| 7,504,019 B2 | 3/2009 | Forrow et al. | |
| 7,754,093 B2 * | 7/2010 | Forrow et al. | ............... 252/62.2 |
| 2005/0067277 A1 | 3/2005 | Pierce et al. | |
| 2006/0201805 A1 * | 9/2006 | Forrow et al. | ............... 204/403.1 |
| 2008/0230384 A1 | 9/2008 | Pierce et al. | |
| 2009/0095625 A1 * | 4/2009 | Forrow | ............... 204/403.14 |
| 2009/0255811 A1 * | 10/2009 | Forrow et al. | ............... 204/403.14 |

FOREIGN PATENT DOCUMENTS

| | | |
|---|---|---|
| EP | 1 146 332 | 10/2001 |
| WO | WO 98/35225 | 8/1998 |
| WO | WO 99/19507 | 4/1999 |

OTHER PUBLICATIONS

Hill et al., Transition Metal Complexes of 1,10-Phenanthroline-5,6-dione as Efficient Mediators for the Regeneration of NAD+ in Enzymatic Synthesis. J. Chem Soc., Chem. Commun. 1993, 1706-07.

Kirk-Othmer Encyclopedia of Chemical Technology, 4th Edition, vol. 9, John Wiley & sons, 1994, pp. 93-95.

Rivera et al., Ruthenium complexes as redox mediators for malate and lactate dehydrogenases. Bioelectrochemistry and Bioenergetics, 34, 1994, pp. 169-175.

Fernandez, Reagentless carbon past phosphate biosensors: preliminary studies, Sensors and Actuators B 47, 1998, 13-20.

Hedenmo et al. Reagentless Amperometric Glucose Dehydrogenase Biosensor Based on Electrocatalytic Oxication of NADH by Osmum Phenathroline Mediator. Analyst, 121, 1996, 1851-95.

Wu et al. "Electrocatalytic Oxidation of NADH at Glassy Carbon Electrodes Modified with Transition Metal Complexes Containing 1,10-phenanthroline-5,6-dione Ligands," Anal. Chem. 68, 3688-96, 1996.

Shabir, et al. "Method, Development and Validation for Determining the Identity, Assay and Purity of 1,10-phenanthroline-5,6-dione by HPLC and LC-MS,".

* cited by examiner

Primary Examiner — Bruce Bell
(74) Attorney, Agent, or Firm — Edward J. Baba; Khin K. Chin; Bozicevic, Field & Francis LLP

(57) ABSTRACT

The present invention provides reagent compositions, and analyte measuring devices and methods that utilize the reagent compositions.

30 Claims, 11 Drawing Sheets

A.

B.

BIOSENSOR HAVING IMPROVED HEMATOCRIT AND OXYGEN BIASES

CROSS-REFERENCE

This application is a continuation of U.S. application Ser. No. 11/420,628 filed May 26, 2006, now U.S. Pat. No. 7,754,093 which is a continuation-in-part application of Ser. No. 10/278,657, filed Oct. 23, 2002, now U.S. Pat. No. 7,501,053, which are incorporated herein by reference in their entirety.

BACKGROUND OF THE INVENTION

All biosensors for determining the concentration of analytes in a sample of blood suffer from hematocrit sensitivity to some degree. The biosensor response decreases as the hematocrit of the sample increases. There is no single reason for this decrease in the signal, though some of the reasons include diminished diffusion of the analyte in the sample and increased solution resistance. One of the methods proposed for the elimination of hematocrit sensitivity is to filter the red cells from the sample. The membrane technology to filter red cells increases both the assay time and measurement imprecision. Oxygen sensitivity has presented a challenge. Biosensors employing the enzyme glucose dehydrogenase are not expected to be oxygen sensitive. However, the oxidation-reduction reactions of the mediator (or coenzyme) could involve free radical intermediates. When these intermediates have long lifetimes, molecular oxygen can quench them, thereby rendering the chemistry sensitive to oxygen tension.

U.S. Pat. Nos. 5,708,247 and 5,951,836 describe a disposable glucose test strip for use in a test meter of the type that receives a disposable test strip and a sample of blood from a patient and performs an electrochemical analysis. The working formulation comprises a filler, an enzyme effective to oxidize glucose, e.g., glucose oxidase, and a mediator effective to transfer electrons from the enzyme. The working formulation is printed over a conductive base layer to form a working electrode. The filler, for example, a silica filler, is selected to have a balance of hydrophobicity and hydrophilicity such that on drying it forms a two-dimensional network on the surface of the conductive base layer. The response of this test strip is claimed to be temperature independent over relevant temperature ranges and is substantially insensitive to the hematocrit of the patient.

In photometric biosensors, a membrane is typically used to separate red cells from a sample of whole blood. The use of a membrane increases the time of response. U.S. Pat. No. 6,271,045 describes a photometric biosensor that employs a correction method to compensate for hematocrit sensitivity. The biosensor comprises a support member that contains a spreading layer and a reagent layer, and a capillary tube in communication with the support layer and spreading layer for transporting a sample of body fluid thereto. A capillary tube is provided on the support member whereby a fluid containing an analyte to be tested is introduced into the tube and flows through the tube to the spreading layer and contacts the reagent layer. In order to compensate for hematocrit level in the case of whole blood, additional sensors can be implemented so that they inspect the capillary tube in the test device, one sensor at the beginning of the capillary channel and one at the end. In this biosensor, whole blood is applied to the capillary channel. The entry flow of whole blood is timed as it moves between sensors. The time that the blood takes to travel the length of the capillary tube is an indication of the hematocrit of the blood. That information is used to correct any shift in reflectance readings of the instrument caused by the hematocrit level. It is also known that the absorbance of hemoglobin can be measured, and the measurement can be used to account for the sensitivity of the measurement to hemoglobin.

The majority of electrochemical biosensors do not use membrane technology; hence, electrochemical biosensors suffer from hematocrit sensitivity. U.S. Pat. No. 6,284,125 describes a biosensor insensitive to hematocrit, where red cells are separated from plasma. U.S. Pat. No. 6,287,451 describes a biosensor that can employ a method in which hematocrit level can be measured electrochemically, and the corrected concentration of an analyte can be determined from the measured concentration of the analyte along with factors that depend on the sensitivity of the biosensor to hematocrit level. The magnitude of the hematocrit sensitivity is dependent on the type of biosensor and on the type of measurement. For example, if the reaction is allowed to go to completion, the lengthy reaction time allows for complete oxidation of the analyte in the sample, thereby making the measurement less sensitive to hematocrit.

U.S. Ser. No. 09/529,617, filed Jun. 7, 2000, incorporated herein by reference, describes $NAD^+$-dependent and $NAD(P)^+$-dependent enzymes having substrates of clinical value, such as glucose, D-3-hydroxybutyrate, lactate, ethanol, and cholesterol. Amperometric electrodes for detection of these substrates and other analytes can be designed by incorporating this class of enzymes and establishing electrical communication with the electrodes via the mediated oxidation of the reduced cofactors NADH and NADPH. $NAD^+$-dependent glucose dehydrogenase can be used as the enzyme and 1,10-phenanthroline-5,6-dione isomer can be used as the mediator. This combination shows hematocrit sensitivity and oxygen sensitivity. The enzyme is not dependent on oxygen (oxygen does not act as a co-substrate as it does with glucose oxidase) and hence is expected to be insensitive to oxygen. However, the mediator reaction appears to be slow and hence is affected by the presence of oxygen. The mediation reaction involves free radical intermediates. If the reaction is slow, the free radical intermediates have longer half-life; hence, the probability of being quenched by molecular oxygen is high. Accordingly, the enzyme mediator combination shows oxygen dependency. The hematocrit bias of 1,10-phenanthroline-5,6-dione mediator is not clearly understood; however, it is speculated that the slow reaction rate of the mediator is responsible for significant hematocrit sensitivity. 4,7-Phenanthroline-5,6-dione does not exhibit as much sensitivity to variations in hematocrit or oxygen as does 1,10-phenanthroline-5,6-dione. However, the structure of 1,10-phenanthroline-5,6-dione renders it easier to synthesize than does the structure of 4,7-phenanthroline-5,6-dione. The starting materials for the synthesis of 1,10-phenanthroline-5,6-dione are much less expensive than are the starting materials for 4,7-phenanthroline-5,6-dione. Additionally, the reaction conditions for the synthesis of 1,10-phenanthroline-5,6-dione are much less severe than are the reaction conditions for 4,7-phenanthroline-5,6-dione. Accordingly, it would be desirable to reduce the sensitivity of 1,10-phenanthroline-5,6-dione to hematocrit sensitivity and oxygen sensitivity.

Glucose monitoring devices are calibrated at normal hematocrit. In samples having a lower hematocrit, the biosensor reads a higher than appropriate blood glucose level, and in samples having a higher hematocrit, the biosensor reads a lower than appropriate blood glucose level.

SUMMARY OF THE INVENTION

This invention involves a reagent composition that includes a mediator, such as an isomer of phenanthroline quinone (PQ), such as 1,10-phenanthroline-5,6-dione or a derivative thereof, a counter anion, and at least one metal ion selected from the group consisting of a transition metal ion, such as, for example, nickel, manganese, iron, osmium, ruthenium, and the like, and heavier alkaline earth metal ion, such as, for example, calcium, barium, and the like. In certain embodiments, the reagent composition further includes an enzyme dependent upon NAD(P)$^+$, such as, for example, glucose dehydrogenase. In such embodiments, when used with a biosensor, the reagent composition provides for improved hematocrit bias and oxygen bias. In addition, the electrodes of biosensors employing this reagent composition provide an accurate clinical response over a hematocrit range that ranges from about 20% to about 70% and over an oxygen tension range that ranges from about 1 kPa to about 20 kPa.

Although oxidation of glucose catalyzed by glucose dehydrogenase is not oxygen sensitive, the mediator can be sensitive to oxygen. The 1,10-phenanthroline-5,6-dione mediator has the structural formula:

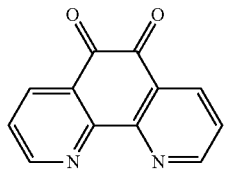

The use of 1,10-phenanthroline-5,6-dione mediator in a glucose biosensor is described in U.S. Ser. No. 09/529,617, filed Jun. 7, 2000, now U.S. Pat. No. 6,736,957, the disclosure of which is incorporated herein by reference in its entirety.

In one aspect, this invention provides a reagent composition for use in an analyte sensing device, wherein the reagent composition includes a mediator, wherein the mediator is 1,10-phenanthroline-5,6-dione or a derivative thereof, at least one metal ion, and a counter anion. The metal ion may be a transition metal ion or a heavier alkaline earth metal ion.

In another aspect, this invention provides a biosensor e.g., in the form of a strip, wherein the biosensor includes:
  an electrode support having at least one electrode thereon; and
  a reagent composition adjacent to the at least one electrode, the reagent composition including an enzyme, a 1,10-phenanthroline-5,6-dione or a derivative thereof as a mediator, a metal ion, wherein the metal ion is a transition metal ion or a heavier alkaline earth metal ion, and a counter anion.

In yet another aspect, this invention provides a biosensor, e.g., in the form of a strip, wherein the biosensor has a working electrode that includes a reagent composition that includes a NAD(P)$^+$-dependent enzyme, 1,10-phenanthroline-5,6-dione or a derivative thereof as a mediator, a metal ion, and a counter anion, wherein the metal ion is a transition metal ion or a heavier alkaline earth metal ion. In one embodiment, the biosensor contains an electrode arrangement that includes two electrodes. The biosensor includes:
  at least one electrode support;
  a first electrode disposed on the electrode support, the first electrode including a working area;
  a second dual-purpose reference/counter electrode disposed on the same electrode support as the first electrode or a different electrode support, the dual-purpose reference/counter electrode being spaced apart from the first electrode. As such, in certain embodiments, wherein the first and second electrodes are on the same electrode support, the electrodes are in a coplanar configuration. In other embodiments, wherein the first and second electrodes are on different electrode supports, the electrodes are in a facing configuration. The term "facing electrodes" refers to a configuration of the working and reference/counter electrodes in which the working surface of the working electrode is disposed in approximate opposition to a surface of the reference/counter electrode.

In yet another embodiment, the biosensor contains an electrode arrangement that includes three electrodes, wherein the biosensor includes:
  at least one electrode support;
  a first electrode disposed on the electrode support, the first electrode being a working electrode;
  a second electrode disposed on the same electrode support as the first electrode or a different electrode support, the second electrode being a reference electrode;
  a reagent composition deposited over the first electrode and second electrode, wherein the reagent composition comprises an enzyme, a mediator, a metal ion, and a counter anion, wherein the mediator is 1,10-phenanthroline-5,6-dione or a derivative thereof, and wherein the metal ion is a transition metal ion or a heavier alkaline earth metal ion; and
  optionally, a third electrode disposed on the same electrode support as the first electrode or a different electrode support, the third electrode being a counter electrode, the counter electrode includes an electrically conductive material.

Embodiments of the invention described herein provide a mediator that is substantially insensitive to hematocrit and oxygen, thereby enabling the use of this mediator in hospital and retail markets, where samples having extreme hematocrit ranges (20% to 70%) and oxygen tensions (neonatal, venous, capillary and arterial) are encountered. A biosensor in the form of a strip employing this mediator can be used for numerous analytes, such as, for example, glucose, ketone bodies, lactate, and alcohol, as well as others.

Embodiments of the invention described herein exhibit several advantages/benefits as compared with other biosensors that are being used for similar purposes. These advantages/benefits may include:
  1. elimination of the requirement of a membrane or any cross-linked network;
  2. the ability to employ a kinetic measurement, and consequently, the elimination of the requirement to drive the reaction to completion, thereby eliminating the hematocrit sensitivity;
  3. the selection of an appropriate reagent combination—enzyme/mediator/metal or enzyme/metal complex of the mediator—is responsible for lower hematocrit sensitivity;
  4. the catalytic and electrochemical activity of the mediator/metal combination or metal complex of the mediator is responsible for oxygen and hematocrit insensitivity;
  5. improved performance is related to the choice of the combination of mediator and metal ion; and
  6. the ability to use a single reagent composition for a working electrode and reference electrode which dispenses with the need for a separate reference electrode layer, thereby reducing the number of manufacturing steps.

Before the present invention is described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and exemplary methods and materials are now described. All publications mentioned herein are incorporated herein by reference to disclose and describe the methods and/or materials in connection with which the publications are cited. It is understood that the present disclosure supercedes any disclosure of an incorporated publication to the extent there is a contradiction.

It must be noted that as used herein and in the appended claims, the singular forms "a", "an", and "the" include plural referents unless the context clearly dictates otherwise. Thus, for example, reference to "a strip" includes a plurality of such cells and reference to "the compound" includes reference to one or more compounds and equivalents thereof known to those skilled in the art, and so forth.

It is further noted that the claims may be drafted to exclude any optional element. As such, this statement is intended to serve as antecedent basis for use of such exclusive terminology as "solely", "only" and the like in connection with the recitation of claim elements, or the use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

BRIEF DESCRIPTION OF THE DRAWINGS

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures.

DETAILED DESCRIPTION OF EMBODIMENTS OF THE INVENTION

Figure 1:
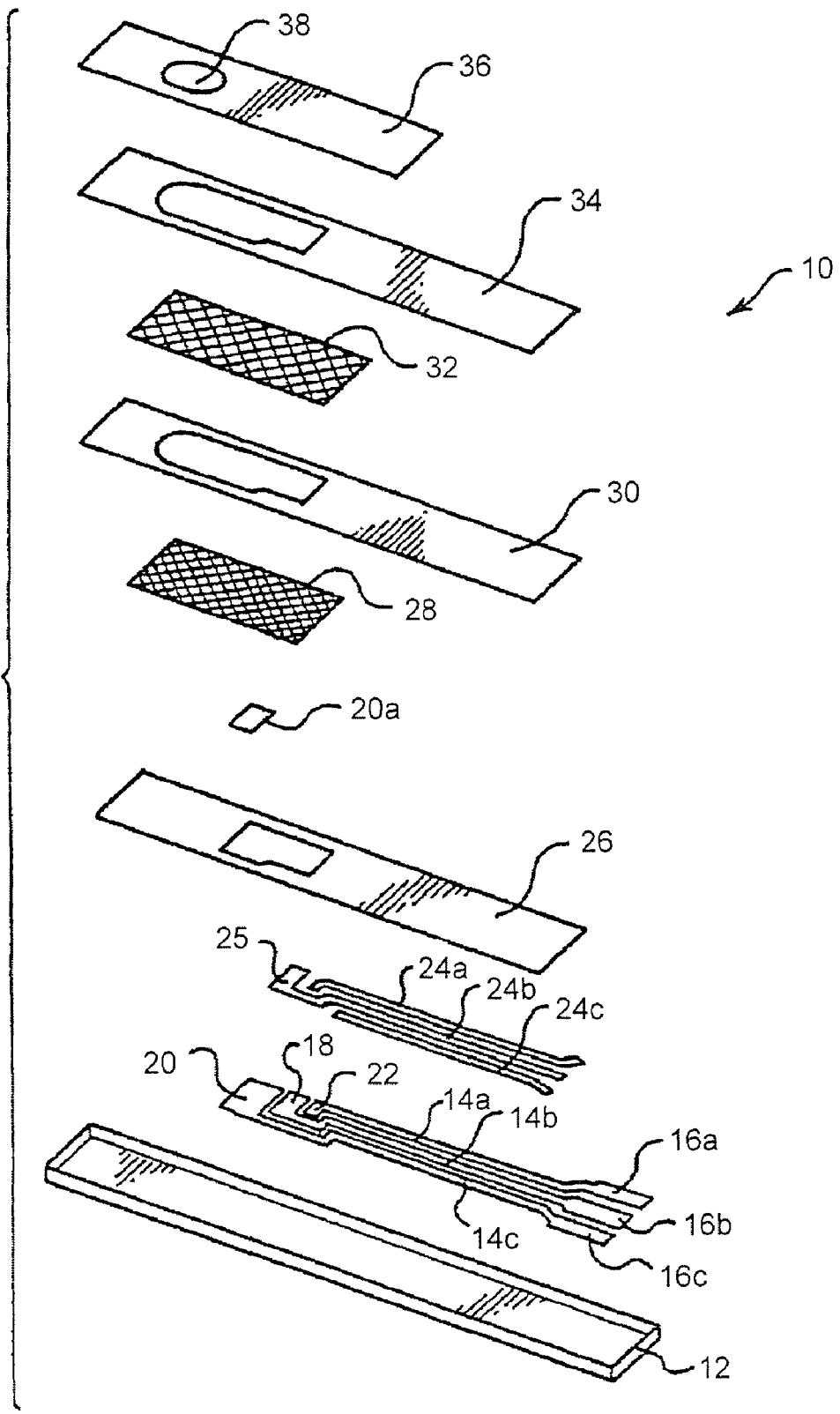
FIG. 1 is a schematic diagram that illustrates a perspective view of a biosensor strip having a working electrode and a dual-purpose reference/counter electrode.

In general, embodiments of the present invention provide reagent compositions that include a mediator, such as an isomer of phenanthroline quinone, 1,10-phenanthroline-5,6-dione or a derivative thereof, a counter anion, and a metal ion. The metal ion can be a transition metal ion or a heavier alkaline earth metal ion. In addition, the present invention also provides biosensors that utilize the reagent composition, as well as methods of using the biosensors for detecting an analyte in a sample.

The structural formula of the mediator 1,10-phenanthroline-5,6-dione is shown below:

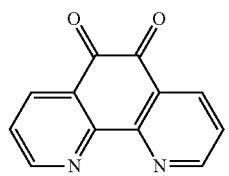

When the mediator is reduced by the enzyme, dimers or oligomers or both are formed on account of intermolecular hydrogen bonding between reduced 1,10-phenanthroline-5, 6-dione molecules. These oligomers are not soluble in the reaction medium and hence are not readily regenerated for continued mediation. Intermolecular hydrogen bonding of a dimer of reduced 1,10-phenanthroline-5,6-dione is shown below.

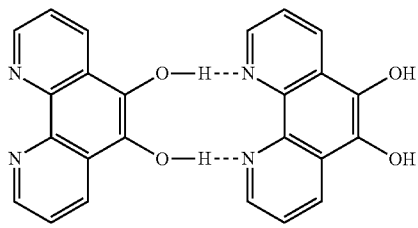

The dimerization or oligomerization can be minimized in several ways. The nitrogen atoms can be blocked by chemical modification. A substituent, e.g., an alkyl group, can be added to one or both of the nitrogen atoms in order to prevent the formation of hydrogen bonds. Preventing the formation of hydrogen bonds also increases the solubility of the mediator in both the oxidized and reduced form. The methyl derivative of 1,10-phenanthroline-5,6-dione shows increased solubility. The compound mediates the oxidation of NADH in the biosensor strip, as described in U.S. Ser. No. 09/529,617, filed Jun. 7, 2000, now U.S. Pat. No. 6,736,957, the disclosure of which is incorporated herein by reference in its entirety. The following structural formula illustrates mono-alkylated 1,10-phenanthroline-5,6-dione, where R represents an alkyl group, such as, for example, —$CH_3$ and X represents an anion such as $BF_4^-$:

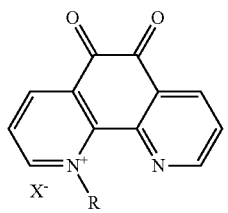

Synthesis of alkylated compounds requires several steps. The alkyl group is introduced after the 1,10-phenanthroline-5,6-dione is formed. The oxidation-reduction properties of alkylated 1,10-phenanthroline-5,6-dione may not be dependent on metal ion concentration, which would indicate that the alkylation process has inhibited the formation of intermolecular hydrogen bonds.

The nitrogen atoms can also be blocked by the formation of a complex having a coordination bond between a ligand and a metal ion. Complexes can be formed prior to being used in a formulation in the strip; alternatively, metal ions can simply be mixed with the ink formulation that contains the mediator.

As used herein, the expression "transition metal" means those elements of a metallic nature that have partially filled d or f shells in any of their commonly occurring oxidation states. The expression "heavier alkaline earth metals" means those elements of a metallic nature that are in the IIA column of the periodic table and that have an atomic number equal to or higher than 20.

The metal ions suitable for use in this invention include, but are not limited to, nickel, manganese, zinc, calcium, iron, ruthenium, cobalt, osmium, nickel, copper, rhenium, rhodium, iridium, chromium, technetium, barium, strontium. The binding efficiencies in these complexes are dependent on the particular metal ion employed. For example, Mn (II) ions provide stronger binding than do Mg (II) ions.

A representative metal complex of 1,10-phenanthroline-5,6-dione is:

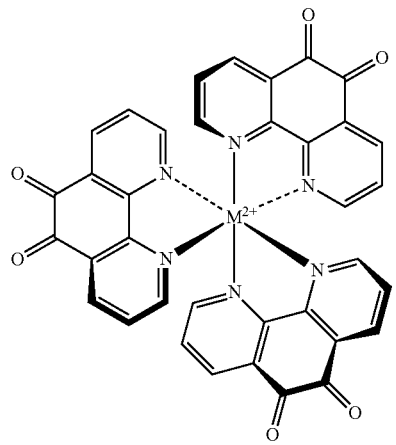

wherein M is selected from the group consisting of nickel, manganese, iron, cobalt, osmium, ruthenium, calcium, strontium, and barium.

In certain embodiments, the metal is nickel and the nickel complex of 1,10-phenanthroline-5,6-dione is:

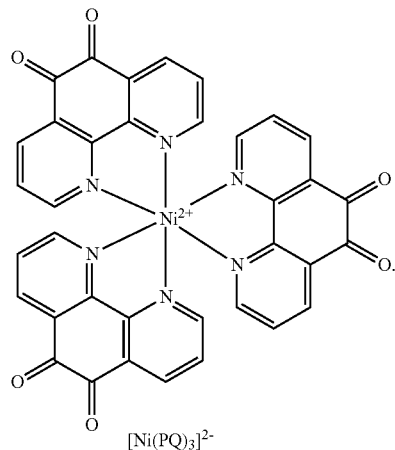

The generic formula of the complex cation is shown below. The ligands a, b, c, and d can represent two 1,10-phenanthroline-5,6-dione molecules or other monodentate ligands, such as, for example, chloride, water, ammonia, or the like, or multidentate ligands, such as, for example, bipyridyl or the like, and M is selected from the group consisting of nickel, manganese, iron, cobalt, osmium, ruthenium, calcium, strontium, and barium.

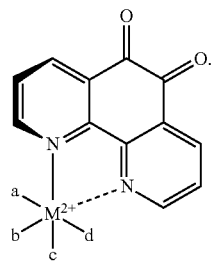

Counter anions suitable for use in this invention include, but are not limited to, a halide, such as chloride, bromide, fluoride, or iodide, a nitrate, a nitrite, a sulfate, a carbonate, a phosphate, a thiocyanate, an acetate, a formate, a citrate, a succinate, an oxalate, a tartrate, a benzoate, an alkyl or aromatic sulfonate, a tungstate, a molybdate, a ferricyanide, a nitroprusside, a tetraphenylborate, an anionic dye and an anionic surfactant.

Figure 2:
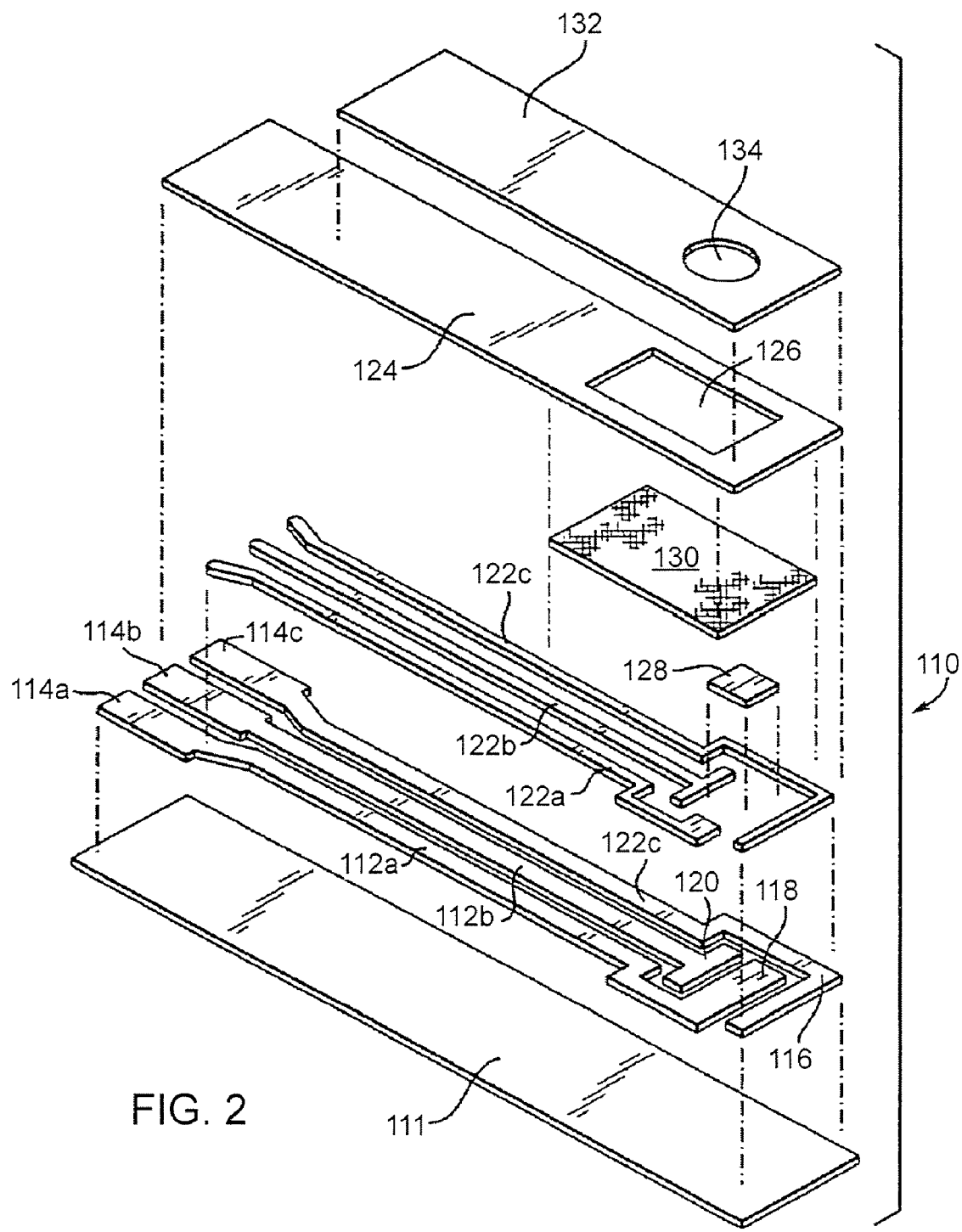
FIG. 2 is a schematic diagram that illustrates a perspective view of a biosensor strip having a working electrode, a reference electrode, and a counter electrode.

Biosensor strips suitable for this invention are illustrated in FIGS. 1 and 2. Referring to FIG. 1, a biosensor strip 10 comprises an electrode support 12, e.g., an elongated strip of polymeric material (e.g., polyvinyl chloride, polycarbonate, polyester, or the like) supports three tracks 14a, 14b, and 14c of electrically conductive ink, e.g., including carbon. These tracks 14a, 14b, and 14c determine the positions of electrical contacts 16a, 16b, and 16c, a dual-purpose reference/counter electrode 18, a working electrode 20, and a trigger electrode 22. The electrical contacts 16a, 16b, and 16c can be inserted into an appropriate measurement device (not shown) for measurement of current.

Each of the elongated portions of the conductive tracks 14a, 14b, and 14c can optionally be overlaid with a track 24a, 24b, and 24c of conductive material, e.g., made of a mixture including silver particles and silver chloride particles. The enlarged exposed area 25 of track 24b overlies the dual-purpose reference/counter electrode 18. A layer of a hydrophobic electrically insulating material 26 further overlies the tracks 14a, 14b, and 14c. The positions of the dual-purpose reference/counter electrode 18, the working electrode 20, the trigger electrode 22, and the electrical contacts 16a, 16b, and 16c are not covered by the layer of hydrophobic electrically insulating material 26. This hydrophobic electrically insulating material 26 serves to prevent short circuits. Because this insulating material is hydrophobic, it can cause the sample to be restricted to the exposed electrodes. An exemplary insulating material is commercially available "POLYPLAST" (Sericol Ltd., Broadstairs, Kent, UK).

Optionally, a first layer of mesh 28, a second insulating layer 30, a second layer of mesh 32, a third insulating layer 34, and a tape 36 can overlay the hydrophobic insulating material. The tape 36 includes a small aperture 38 to allow access of the applied sample to the underlying layers of mesh 28 and 32. The second insulating layer 30 and the third insulating layer 34 include openings to allow access of the applied sample to the underlying layers of mesh 28 and 32.

The working electrode 20 includes a layer of conductive material containing a working area 20a. The working area 20a may be formed from a reagent composition, which is added (e.g., printed) on the layer of conductive material of the working electrode 20. The reagent composition includes a mixture of an oxidation-reduction mediator, a metal ion, a counter anion, an enzyme, and, optionally, a conductive material.

The working area 20a may be formed from a printing ink that includes the reagent composition described above, that includes a mixture of an enzyme, an oxidation-reduction mediator, a counter anion, a metal ion, and, optionally, a conductive material. Alternatively, instead of an enzyme, the working area 20a can contain a substrate that is catalytically reactive with an enzyme to be assayed. The reagent composition is then applied to the working electrode 20 and the dual-purpose reference/counter electrode 18 as discrete areas of fixed length. In certain embodiments, the conductive material includes particles of carbon and the oxidation-reduction mediator comprises 1,10-phenanthroline-5,6-dione.

In other embodiments, the electrodes are formed on one or more electrode supports by any suitable method including chemical etching, laser ablation, photolithography, and the like. In general, the electrode support is formed from an insulating material, so that it will not provide an electrical connection between the electrodes of the electrode set. Examples include glass, ceramics and polymers. In certain embodiments, the electrode substrate is a flexible polymer, such as a polyester or polyimide.

For example, in the laser ablation process, the metallic layer may be ablated into an electrode pattern. Furthermore the patterned metallic layer may be coated or plated with additional metal layers. For example, the metallic layer may be copper, which is then ablated with a laser, into an electrode pattern; subsequently, the copper may be plated with a titanium/tungsten layer, and then a gold layer, to form the desired electrodes. In certain embodiments, however, only a single layer of gold is used, which is directly in contact with the electrode substrate. In such embodiments, the reagent composition can be positioned adjacent to the electrode(s).

In one such method, one or more channels are formed in the substrate, for example by an embossing process using an embossing die or roller. Other methods for forming the channels, such as the use of a laser, or photolithography and etching of the substrate can also be employed if desired.

The conductive material may contain pure metals or alloys, or other materials which are metallic conductors. Examples include aluminum, carbon (such as graphite), cobalt, copper, gallium, gold, indium, iridium, iron, lead, magnesium, mercury (as an amalgam), nickel, niobium, osmium, palladium, platinum, rhenium, rhodium, selenium, silicon (such as highly doped polycrystalline silicon), silver, tantalum, tin, titanium, tungsten, uranium, vanadium, zinc, zirconium, mixtures thereof, and alloys or metallic compounds of these elements. In certain embodiments, the conductive material includes carbon, gold, platinum, palladium, iridium, or alloys of these metals, since such noble metals and their alloys are unreactive in biological systems.

The reagent composition includes an aqueous suspension of the conductive material, a redox mediator, a metal ion, and a counter anion. For the working electrode 20, the reagent composition also includes an enzyme. For example, when the analyte to be measured is glucose in blood, the enzyme is glucose dehydrogenase, and the redox mediator is a 1,10-phenanthroline-5,6-dione. In the alternative, for the working electrode 20, the printing ink can include a substrate in lieu of an enzyme when the analyte to be measured is an enzyme.

In certain embodiments, the reagent composition can be screen-printed. In such embodiments, the reagent composition can further include a polysaccharide (e.g., a guar gum or an alginate), a hydrolyzed gelatin, an enzyme stabilizer (e.g., glutamate or trehalose), a film-forming polymer (e.g., a polyvinyl alcohol), a conductive filler (e.g., carbon), a defoaming agent, a buffer, or a combination of the foregoing.

The electrodes cannot be spaced so far apart that both the working electrode 20 and the dual-purpose reference/counter electrode 18 cannot be covered by the sample. In certain embodiments, the length of the path to be traversed by the sample (i.e., the sample path) is kept as short as possible in order to minimize the volume of sample required. The maximum length of the sample path can be as great as the length of the biosensor strip. However, the corresponding increase in resistance of the sample limits the length of the sample path to a distance that allows the necessary response current to be generated. The resistance of the sample is also influenced by the distance from the edge of the area of the dual-purpose reference/counter electrode 18 to the edge of the working area of the working electrode 20. Reducing this distance by positioning the dual-purpose reference/counter electrode 18 downstream from the working electrode 20 increases the resistance of the sample. Positioning the electrodes contiguously is conventional.

The trigger electrode 22 can be placed downstream of the reference electrode. The trigger electrode 22 can be used to determine when the sample has been applied to the strip, thereby activating the assay protocol. See U.S. Ser. No. 09/529,617, filed Jun. 7, 2000, now U.S. Pat. No. 6,736,957, the disclosure of which is incorporated herein by reference in its entirety.

A biosensor strip 110 suitable for this invention is illustrated in FIG. 2. Referring to FIG. 2, an electrode support 111, such as an elongated strip of polymeric material (e.g., polyvinyl chloride, polycarbonate, polyester, or the like) supports three tracks 112a, 112b, and 112c of electrically conductive ink, such as carbon. These tracks 112a, 112b, and 112c determine the positions of electrical contacts 114a, 114b, and 114c, a reference electrode 116, a working electrode 118, and a counter electrode 120. The electrical contacts 114a, 114b, and 114c are insertable into an appropriate measurement device (not shown) for measurement of current.

Each of the elongated portions of the conductive tracks 112a, 112b, and 112c can optionally be overlaid with a track 122a, 122b, and 122c of conductive material, for example made of a mixture including silver particles and silver chloride particles. The enlarged exposed area of track 122b overlies the reference electrode 116. A layer of a hydrophobic electrically insulating material 124 further overlies the tracks 112a, 112b, and 112c. The positions of the reference electrode 116, the working electrode 118, the counter electrode 120, and the electrical contacts 114a, 114b, and 114c are not covered by the layer of hydrophobic electrically insulating material 124. This hydrophobic electrically insulating material 124 serves to prevent short circuits. The layer of hydrophobic electrically insulating material 124 has an opening 126 formed therein. This opening 126 provides the boundary for the reaction zone of the biosensor strip 110. Because this insulating material is hydrophobic, it can cause the sample to be restricted to the portions of the electrodes in the reaction zone. The working electrode 118 comprises a layer of a nonreactive electrically conductive material on which is deposited a layer 128 containing a reagent composition for carrying out an oxidation-reduction reaction. At least one layer of mesh 130 overlies the electrodes. This layer of mesh 130 protects the printed components from physical damage. The layer of mesh 130 also helps the sample to wet the electrodes by reducing the surface tension of the sample, thereby allowing it to spread evenly over the electrodes. A cover 132 encloses the surfaces of the electrodes that are not in contact with the electrode support 111. This cover 132 is a liquid impermeable membrane. The cover 132 includes a small aperture 134 to allow access of the applied sample to the underlying layer of mesh 130.

The reagent composition 128 is deposited on that portion of the electrically conductive material of the working electrode 118 where the oxidation-reduction reaction is to take place when a sample is introduced to the biosensor strip 110. In such embodiments, the reagent composition 128 can be applied to the working electrode 118 as a discrete area having a fixed length. Typical analytes of interest include, for example, glucose and ketone bodies. Typical non-reactive electrically conductive materials include, for example, carbon, platinum, palladium, iridium, and gold. A semiconducting material such as indium doped tin oxide can be used as the non-reactive electrically conductive material. In certain embodiments, the reagent composition includes a mixture of an oxidation-reduction mediator and an enzyme. Alternatively, instead of an enzyme, the reagent composition can contain a substrate that is catalytically reactive with an enzyme to be assayed. In the biosensor strips of this invention, the reagent(s) are applied in the form of a composition containing particulate material and having binder(s), and, accordingly, does not dissolve rapidly when subjected to the sample. In view of this feature, the oxidation-reduction reaction will occur at the interface of working electrode 118 and the sample. The glucose molecules diffuse to the surface of the working electrode 118 and react with the enzyme/mediator mixture.

In addition to being applied to the working electrode 118, a layer of the reagent composition can be applied to any of the other electrodes, such as the reference electrode when desired, as a discrete area having a fixed length.

Other possible biosensor strip designs include those in which the mesh layer 130 is eliminated, and the flow channel is of such dimensions that the biosensor strip takes up a liquid sample by capillary attraction. See U.S. Ser. No. 10/062,313, filed Feb. 1, 2002, incorporated herein by reference.

The mediator can be used for any NAD(P)$^+$ dependent enzyme. Representative examples of these enzymes are set forth in Table 1.

TABLE 1

| E.C. (enzyme classification) Number | Enzyme name |
|---|---|
| 1.1.1.1 | Alcohol dehydrogenase |
| 1.1.1.27 | Lactate dehydrogenase |
| 1.1.1.31 | β-hydroxybutyrate dehydrogenase |
| 1.1.1.49 | Glucose-6-phosphate dehydrogenase |
| 1.1.1.47 | Glucose dehydrogenase |
| 1.2.1.46 | Formaldehyde dehydrogenase |
| 1.1.1.37 | Malate dehydrogenase |
| 1.1.1.209 | 3-hydroxysteroid dehydrogenase |

Other enzyme systems that can be used with the mediator include, but are not limited to, oxidases (glucose oxidase, cholesterol oxidase, lactate oxidase). Formulations for screen-printing reagents on an electrode comprise the components set forth in Table 2 and Table 3, where % means % by weight.

TABLE 2

| | |
|---|---|
| (NAD)P$^+$ dependent enzyme (such as glucose dehydrogenase) | 200 to 4000 units per gram |
| Nicotinamide adenine dinucleotide (NAD) | 5 to 30% |
| 1,10-phenanthroline-5,6-dione | 0.1 to 1.5% |
| Filler (such as carbon or silica) | 10 to 30% |
| Binder (such as hydroxyethyl cellulose or guar gum or alginate) | 0.01 to 0.5% |
| Protein stabilizer (such as trehalose or bovine serum albumin) | 0.01 to 2% |
| Metal ion | 0.1 to 10% |
| Buffers and other electrolytes | 1 to 10% |

TABLE 3

| | |
|---|---|
| (NAD)P$^+$ dependent enzyme (such as glucose dehydrogenase) | 200 to 4000 units per gram |
| Nicotinamide adenine dinucleotide (NAD) | 5 to 30% |
| Metal complex of 1,10-phenanthroline-5,6-dione | 0.1 to 1.5% |
| Filler (such as carbon or silica) | 10 to 30% |
| Binder (such as hydroxyethyl cellulose or guar gum or alginate) | 0.01 to 0.5% |
| Protein stabilizer (such as trehalose or bovine serum albumin) | 0.01 to 15% |
| Buffers and other electrolytes | 1 to 10% |

The performance of biosensors for determining electrochemical ketone bodies can also be enhanced with the use of this chemistry. A typical formulation for determination of ketone bodies is shown in Table 4.

TABLE 4

| | |
|---|---|
| β-hydroxybutyrate dehydrogenase | 200 to 4000 units per gram |
| Nicotinamide adenine dinucleotide (NAD) | 5 to 30% |
| 1,10-phenanthroline-5,6-dione | 0.1 to 1.5% |
| Filler (such as carbon or silica) | 10 to 30% |
| Binder (such as hydroxyethyl cellulose or guar gum or alginate) | 0.01 to 0.5% |
| Protein stabilizer (such as trehalose or bovine serum albumin) | 0.01 to 2% |
| Metal ion | 0.1 to 10% |
| Buffers and other electrolytes | 1 to 10% |

In general, NAD(P)$^+$-dependent enzymes react with substrate according to the relationship $$RH_2 + NAD(P)^+ \rightarrow R + NAD(P)H + H^+$$

NAD(P)H is oxidized back to NAD(P)$^+$ by the mediator described in this invention. The rate of this oxidation reaction is slower than that of other isomers (1,7-phenanthroline-5,6-dione and 4,7-phenanthroline-5,6-dione). This slow reaction rate prevents rapid regeneration of the coenzyme and hence makes it susceptible to variation in hematocrit or oxygen in the sample. The mediator will have higher probability of reacting with molecular oxygen and hence become sensitive to oxygen. The diffusion of the mediator in the sample is affected by the hematocrit variation and slow reacting mediator will be more affected by restricted mobility compared to a fast reacting mediator. The metal ions described herein allow rapid regeneration of the coenzyme and hence makes it less susceptible to variation in hematocrit or oxygen in the sample.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1

Figure 3:
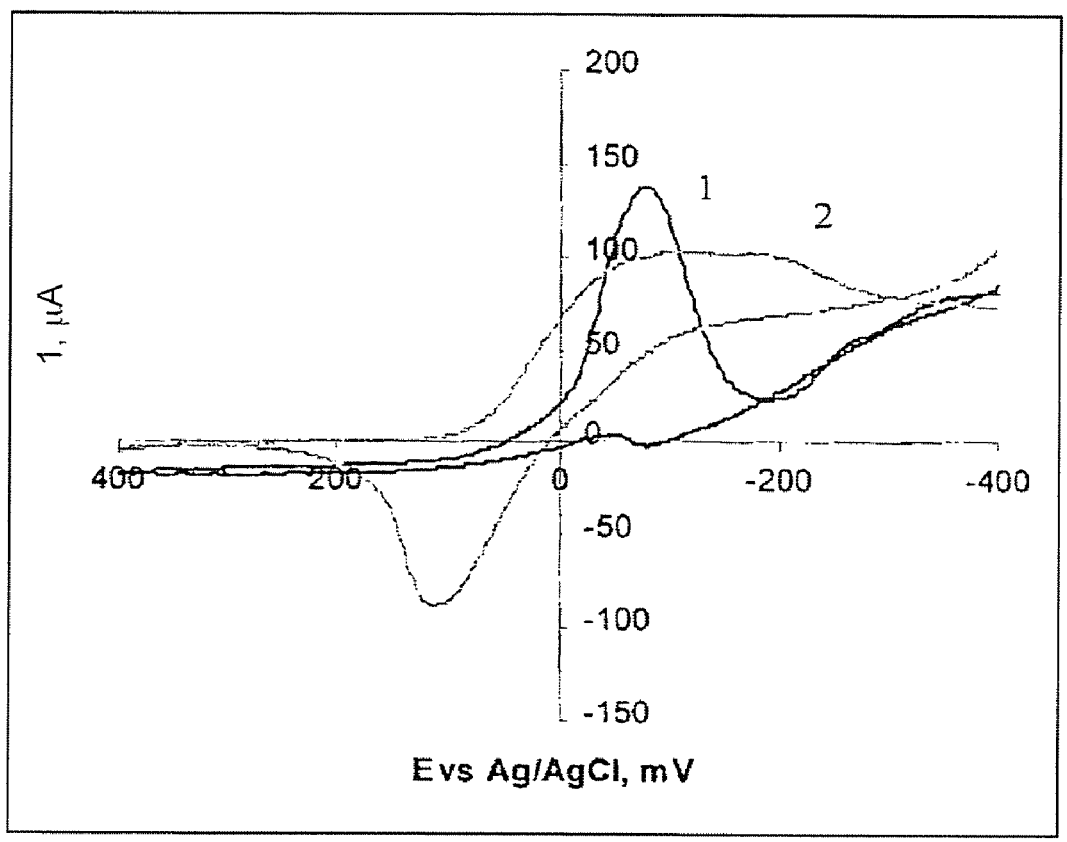
FIG. 3 is a graph showing electrochemical properties of 1,10-phenanthroline-5,6-diose in the absence of manganese chloride (Curve 1) and in the presence of manganese chloride (Curve 2).

Metal ion is required for efficient mediation of NADH oxidation by 1,10-phenanthroline-5,6-dione. In solution, 1,10-phenanthroline-5,6-dione does not show any electrochemical oxidation at physiological pH conditions. In the presence of a metal ion such as manganese, the mediator shows both oxidation and reduction current. FIG. 3 shows the electrochemical properties of 1,10-phenanthroline-5,6-dione in the presence of manganese chloride (Curve 2) and in the absence of manganese chloride (Curve 1).

The concentration of the metal ion required for the optimal performance of the biosensor depends on the binding constant of the metal and the 1,10-phenanthroline-5,6-dione. The efficiency of complex formation and stability of the complex is dependent on the metal ion. For example, only 10 mM manganese chloride is sufficient to achieve the performance that is achieved by a 360 mM magnesium chloride for 30 mM of 1,10-phenanthroline-5,6-dione in the formulation. Ten (10) mM manganese chloride corresponds to a ratio of one (1) metal ion to three (3) 1,10-phenanthroline-5,6-dione molecules in the formulation that forms the metal complex. The binding constant of Pb (II) with 1,10-phenanthroline-5,6-dione is greater than the binding constant of Mn (II) or Mg (II) with 1,10-phenanthroline-5,6-dione; however, the enzyme is inactivated by Pb (II). Mediation of NADH oxidation by 1,10-phenanthroline-5,6-dione in the presence of other transition metal ions and heavier alkaline earth metal ions has been demonstrated.

Transition metal ions and heavier alkaline earth metal ions can also be used as complexes for the mediation of NADH oxidation. The performance of the free ion Mn (II) mixed in the formulation is identical to the performance of the complex that is formed before it is added to the ink formulation.

Figure 4:
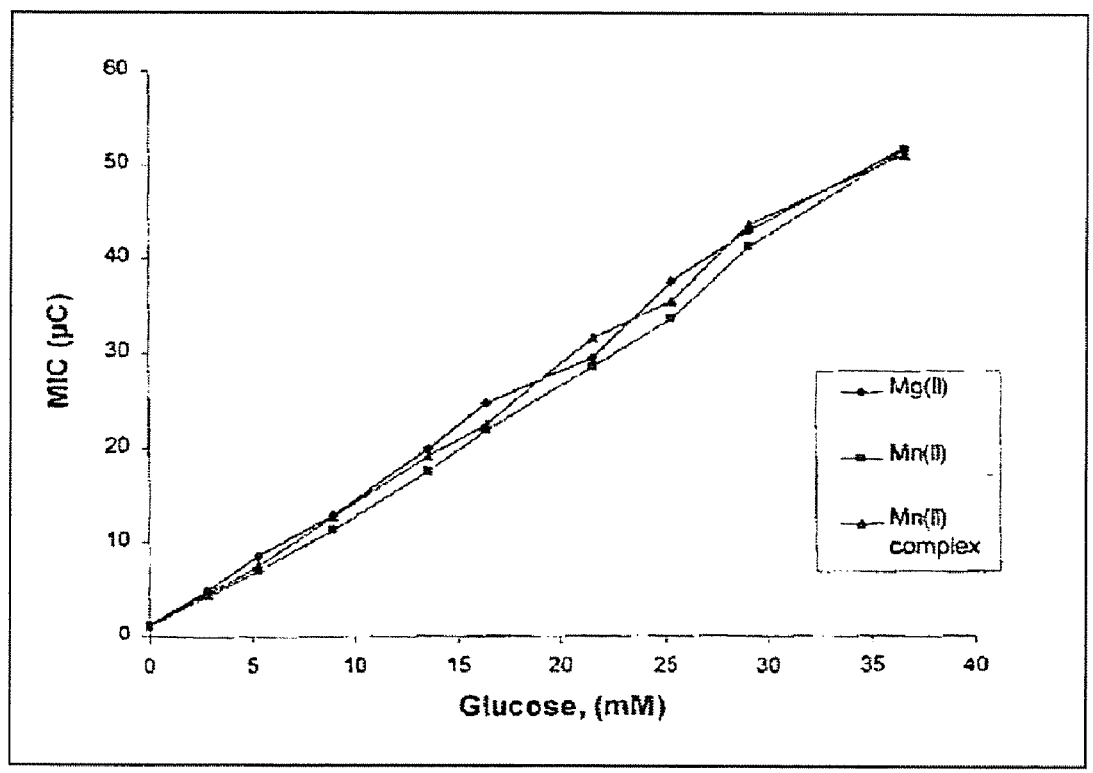
FIG. 4 is a graph showing the response of a biosensor as a function of the concentration of glucose for three formulations involving the mediator.
Figure 5:
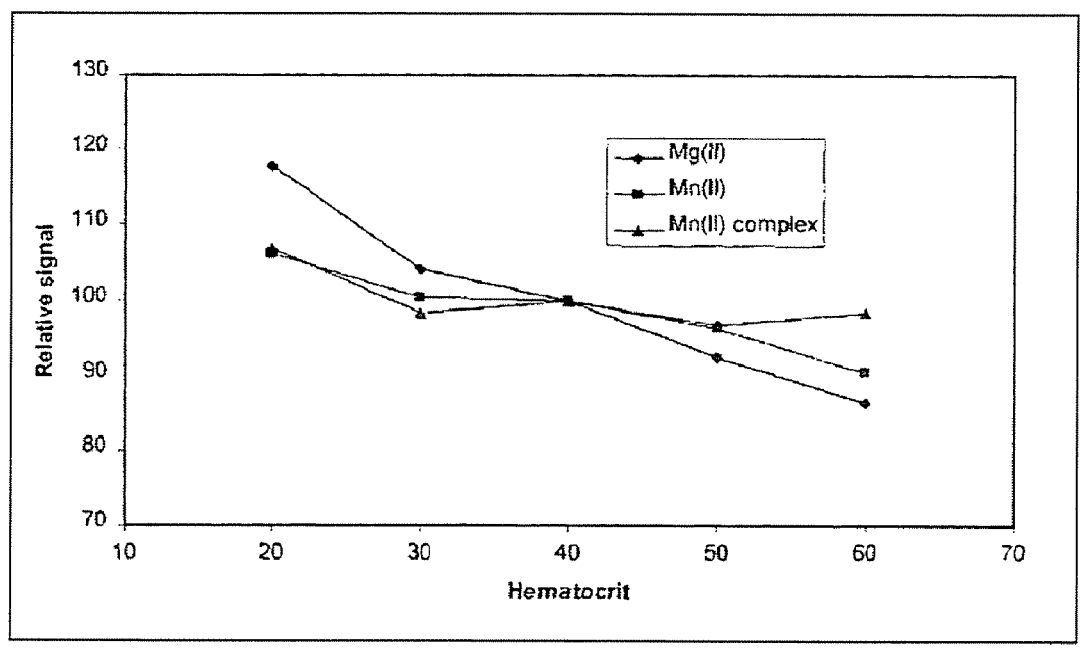
FIG. 5 is a graph showing the relative signals of biosensors for of glucose (15 mM sample) as a function of hematocrit for three formulations involving the mediator. The data are normalized to the signal at 40% hematocrit.
Figure 6:
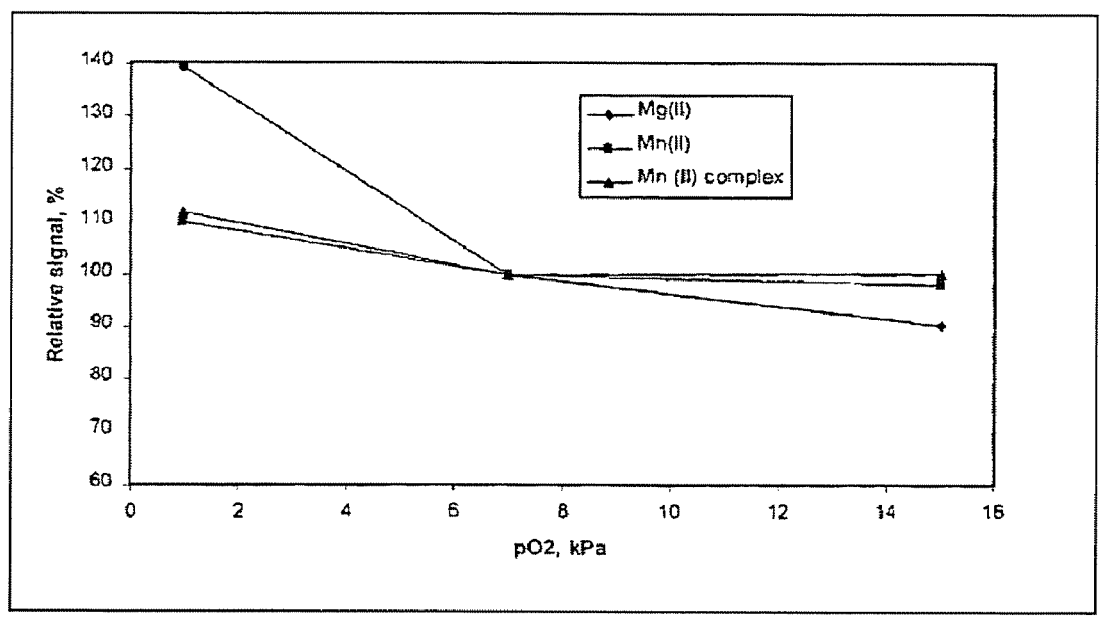
FIG. 6 is a graph showing the relative oxygen sensitivities of biosensors for three formulations involving the mediator. The data are normalized to 7 kPa.

The hematocrit and oxygen bias of formulations containing Mn (II) are significantly improved compared to the formulations containing Mg (II). FIG. 4 shows correlation of biosensor response as a function of concentration of glucose for the three mediation chemistries. FIG. 5 shows the relative signals of a 15 mM sample as a function of hematocrit normalized to the signal at 40% hematocrit. FIG. 6 shows oxygen sensitivities of the biosensors with three chemistries normalized to 7 kPa. Similar hematocrit and oxygen bias advantages are seen with the Fe (II) complex of 1,10-phenanthroline-5,6-dione. In other words, using a transition metal ion or a heavier alkaline earth metal ion in the formulation improves the electrochemical properties of the compound. Some of the transition metal ions and heavier alkaline earth metal ions show improved oxygen and hematocrit sensitivities as compared with other transition metal ions and heavier alkaline earth metal ions.

The complexes were either formed prior to use in the strip or the metal ions were mixed with the ink. The metal ions used were transition metal ions and heavier alkaline earth metal ions.

Example 2

Synthesis

Ultra-soluble [Ni(PQ)$_3$]$^{2+}$ salts were prepared by adding solid PQ (3-fold excess) to a solution of the appropriate nickel (II) salt. PQ was dissolves to form the Ni(II) complex. The solution was filtered and then freeze-dried to give the solid [Ni(PQ)$_3$]$^{2+}$ salt.

Slightly soluble [Ni(PQ)$_3$]$^{2+}$ salts were prepared by adding the appropriate anion to a solution of an ultra-soluble [Ni(PQ)$_3$]$^{2+}$ salt, e.g., [Ni(PQ)$_3$]Cl$_2$ then filtering the resulting precipitated product followed by drying.

Aqueous Solubility

Solubility tests in water were performed on the new redox mediators in comparison with the standard PQ mediators. Of the new mediators prepared so far, the fluoride, chloride, bromide, iodide, nitrate, sulfate and acetate salts of [Ni(PQ)$_3$]$^{2+}$ were found to have aqueous solubility in excess of 20 mg/ml (2%) compared to <4 mg/ml (<0.4%) for the standard PQ mediators. As expected, the perchlorate, tetrafluoroborate and hexafluorophosphate salts of [Ni(PQ)$_3$]$^{2+}$ had very low solubility in water (<0.5 mg/ml). A summary of the results is provided in Table 5.

TABLE 5

| Mediator | Solubility in Water |
| --- | --- |
| [Ni(PQ)$_3$]Cl$_2$ | >400 mg/ml (>40%) |
| [Ni(PQ)$_3$]Br$_2$ | 20 mg/ml (2%) |
| [Ni(PQ)$_3$]I$_2$ | 20 mg/ml (2%) |
| [Ni(PQ)$_3$]F$_2$ | >200 mg/ml (>20%) |
| [Ni(PQ)$_3$](NO$_3$)$_2$ | 50 mg/ml (5%) |
| [Ni(PQ)$_3$](ClO$_4$)$_2$ | <0.5 mg/ml (<0.05%) |
| [Ni(PQ)$_3$](PF$_6$)$_2$ | <0.5 mg/ml (<0.05%) |
| [Ni(PQ)$_3$](BF$_4$)$_2$ | <0.5 mg/ml (<0.05%) |
| [Ni(PQ)$_3$](O$_2$CCH$_3$)$_2$ | >500 mg/ml (>50%) |
| [Ni(PQ)$_3$]SO$_4$ | >500 mg/ml (>50%) |
| PQ | 2 mg/ml (0.2%) |
| [Mn(PQ)$_3$]Cl$_2$ | 4 mg/ml (0.4%) |
| [Fe(PQ)$_3$]Cl$_2$ | >200 mg/ml (>20%) |

Reagent Film Homogeneity

Figure 7:
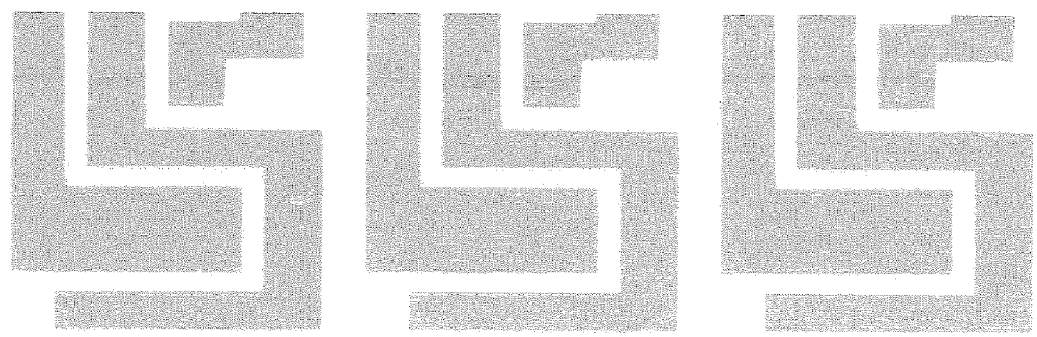
FIG. 7 is a comparison of the reagent film homogeneity of ultra-soluble mediator $[Ni(PQ)_3]Cl_2$ of the present invention with the PQ mediator. Panel A is an image of a reagent film derived from a solution containing 3% $[Ni(PQ)_3]Cl_2$. Panel B is an image of a reagent composition derived from a suspension containing 3% PQ.
Figure 7:
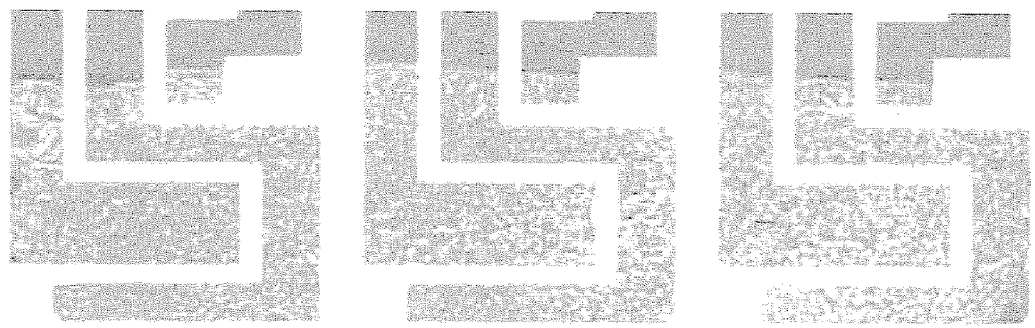

A comparison of ultra-soluble mediator [Ni(PQ)$_3$]Cl$_2$ of the present invention with the standard PQ mediator was also performed. FIG. 7 provides results of the comparison of the reagent film homogeneity of ultra-soluble mediator [Ni(PQ)$_3$]Cl$_2$ of the present invention with the PQ mediator. Panel A is an image of a reagent film derived from a solution containing 3% [Ni(PQ)$_3$]Cl$_2$. Panel B is an image of a reagent composition derived from a suspension containing 3% PQ. As shown in FIG. 7, the [Ni(PQ)$_3$]Cl$_2$ mediator provides a uniform reagent composition with no visible sign of solid particles or crystals whereas the reagent composition derived from the PQ mediator display a non-even distribution of solid particles.

Electrochemistry

Figure 8:
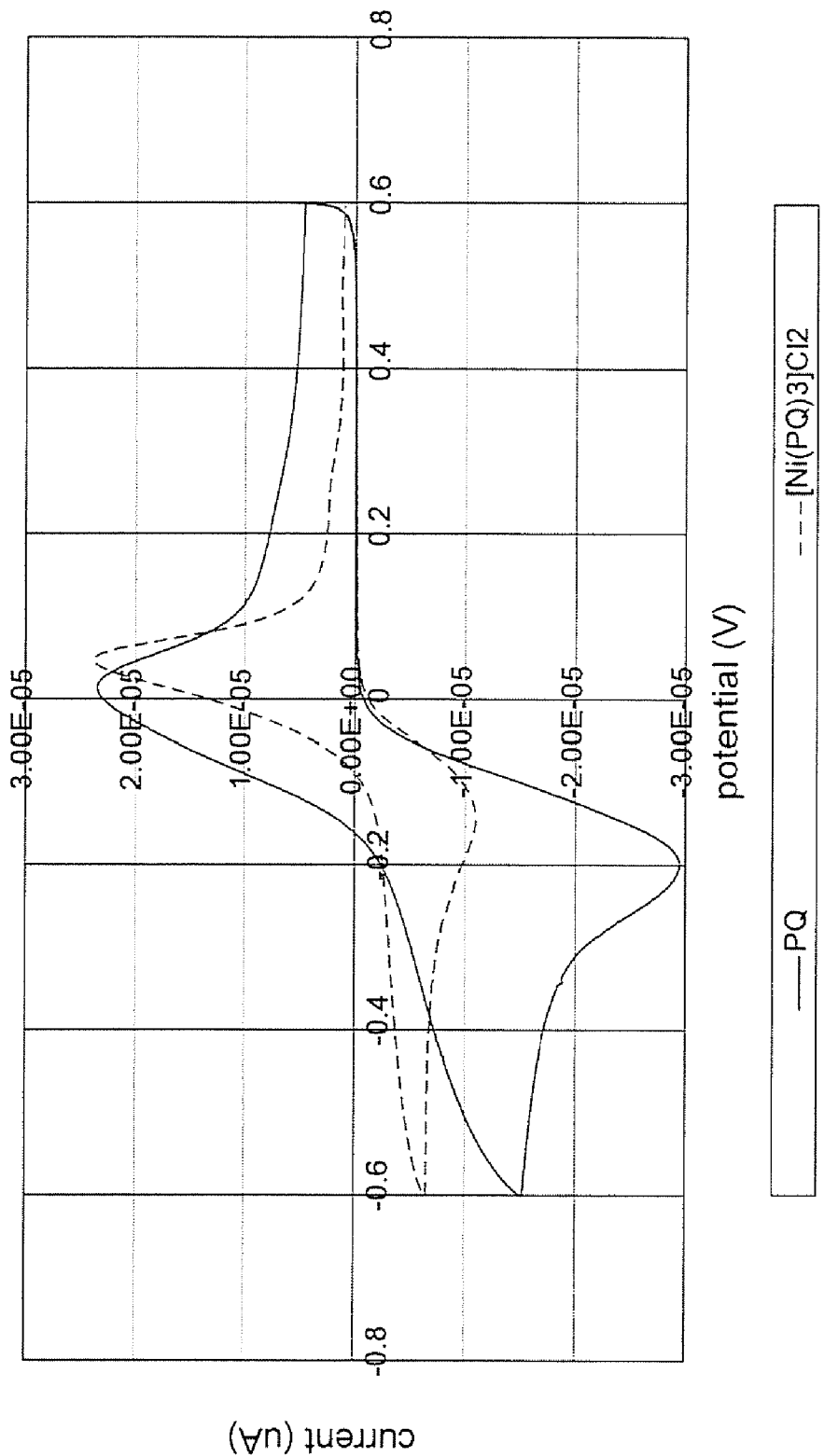
FIG. 8 is a graph showing the cyclic voltammetry properties of PQ (solid line) and $[Ni(PQ)_3]Cl_2$ (broken line) on blank screen-printed carbon electrodes versus Ag/AgCl reference. The graph shows that the $[Ni(PQ)_3]Cl_2$ mediator of the present invention has a similar oxidation potential (Eox) to the PQ mediator.

The electrochemistry properties the ultra-soluble mediator [Ni(PQ)$_3$]Cl$_2$ of the present invention and the standard PQ mediator were also determined. The graph of FIG. 8 shows the cyclic voltammetry properties of PQ (solid line) as compared to the properties of [Ni(PQ)$_3$]Cl$_2$ (broken line) on blank screen-printed carbon electrodes versus Ag/AgCl reference. The graph shows that the [Ni(PQ)$_3$]Cl$_2$ mediator of the present invention has a similar oxidation potential (Eox) to the standard PQ mediator.

Examples of Electrode Calibrations with Different Enzymes

A stock aqueous reagent composition for use in analyte sensing was prepared containing the following:
- 3.4% [Ni(PQ)$_3$]Cl$_2$,
- 2% polymer,
- 4.7% trehalose,
- 0.7% MgCl$_2$, and
- 0.7% NAD (pH adjusted to 7).

Various enzymes were then added and the resulting solution was used to coat gold electrodes which were dried for 3 min at 75° C. Pre-formed capillary fill cells were then applied and the strips trimmed to size. Testing was performed using the appropriate substrate/analyte solutions in PBS. Test parameters included the following: 0 sec delay, +200 mV applied potential (vs. mediator redox couple—biamperometry), 100 Hz sampling time, manual assay start. Electrode calibrations were performed at 1, 2, and 3 sec assay times. The working electrode reaction was based on:

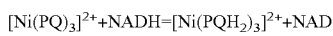

[Ni(PQ)$_3$]$^{2+}$+NADH=[Ni(PQH$_2$)$_3$]$^{2+}$+NAD

Then [Ni(PQH$_2$)$_3$]$^{2+}$ is oxidized to [Ni(PQ)$_3$]$^{2+}$ at the electrode. The reference electrode reaction was based on the reduction of [Ni(PQ)$_3$]$^{2+}$ to [Ni(PQH$_2$)$_3$]$^{2+}$.

Figure 9:
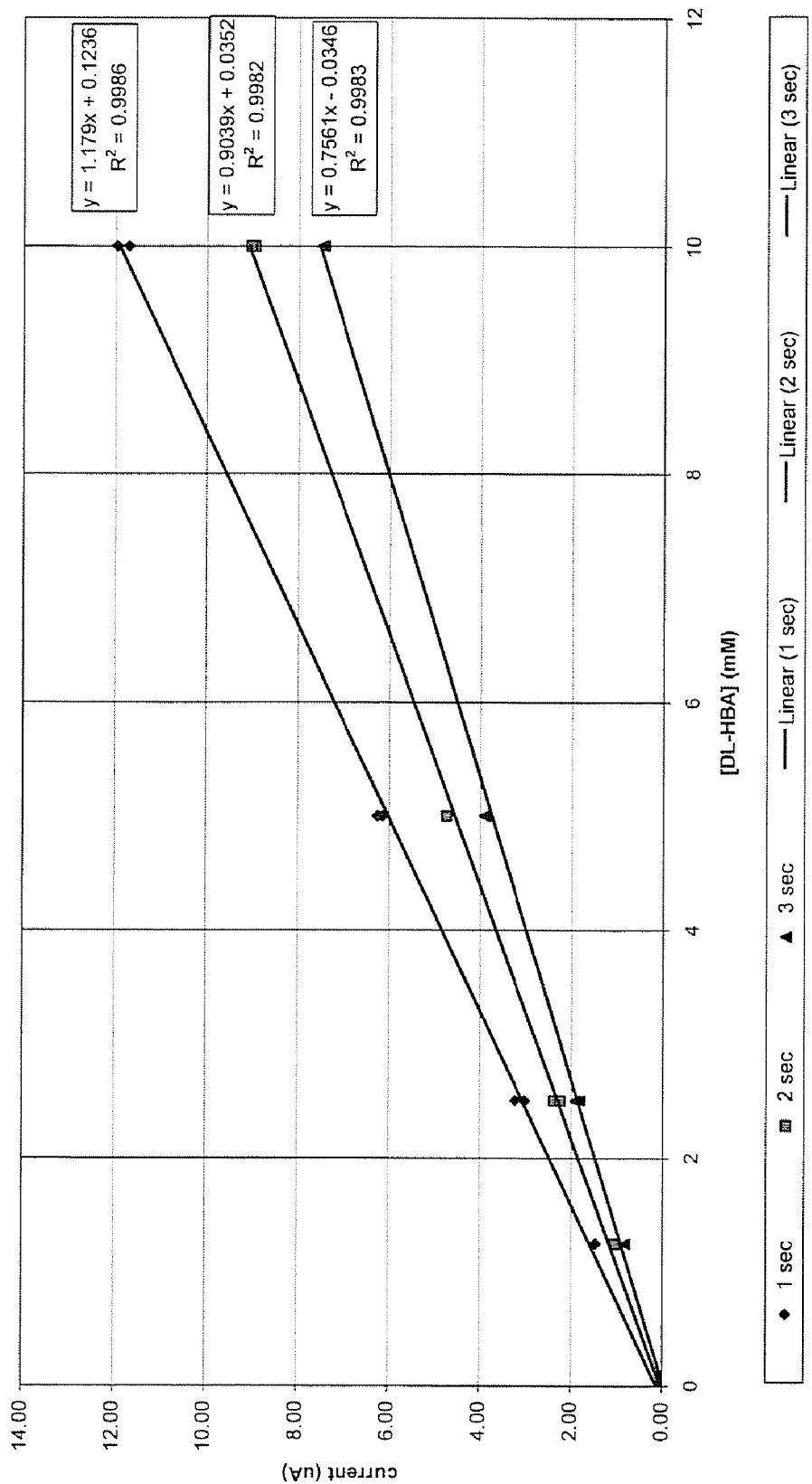
FIG. 9 is a graph showing the electrode calibrations at 1, 2, and 3 second assay times with $[Ni(PQ)_3]Cl_2$ and D-3-hydroxybutyrate dehydrogenase (HBDH).
Figure 10:
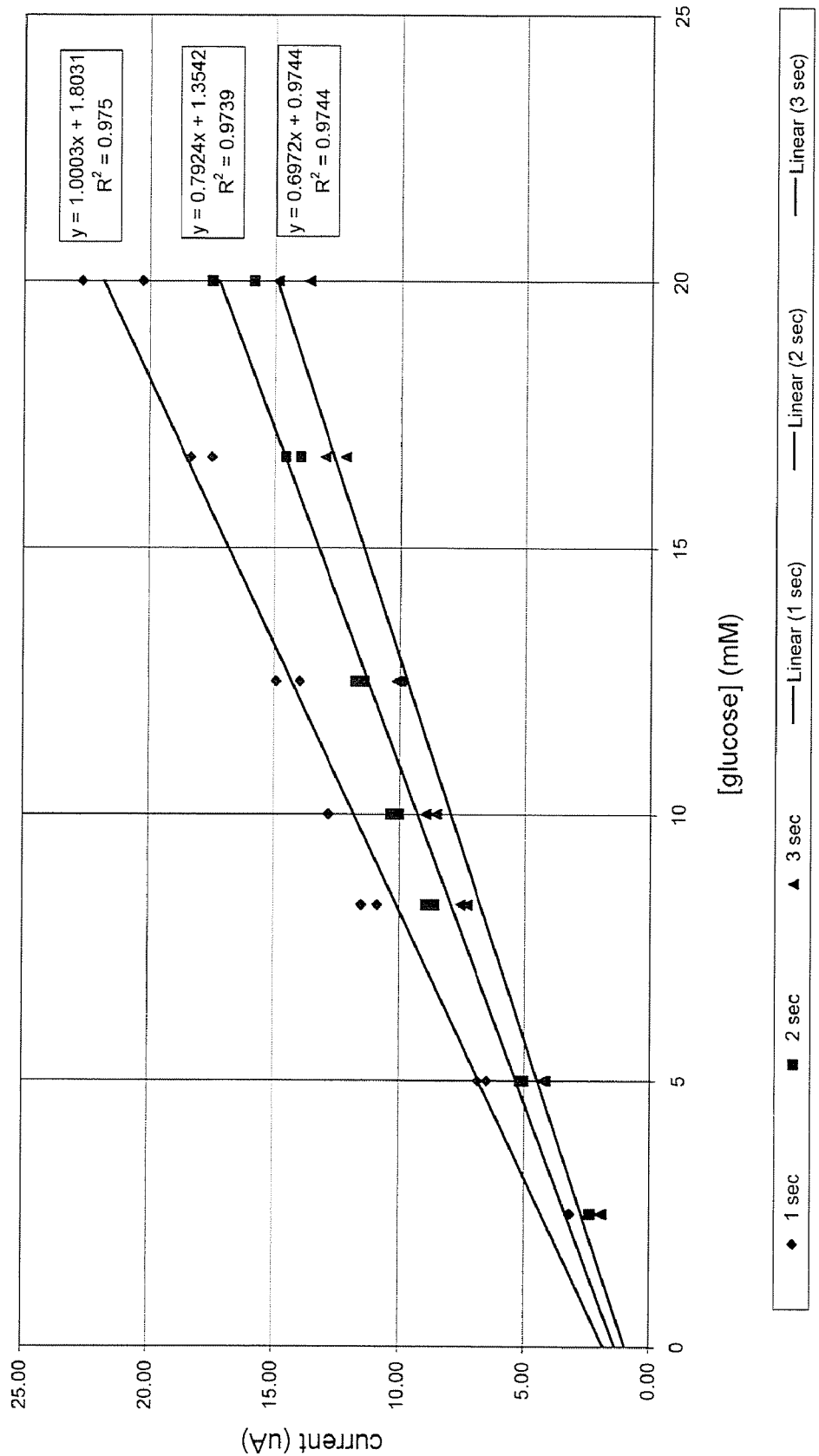
FIG. 10 is a graph showing the electrode calibrations at 1, 2, and 3 second assay times with $[Ni(PQ)_3]Cl_2$ and glucose dehydrogenase with nicotinamide adenine dinucleotide (GDH/NAD).
Figure 11:
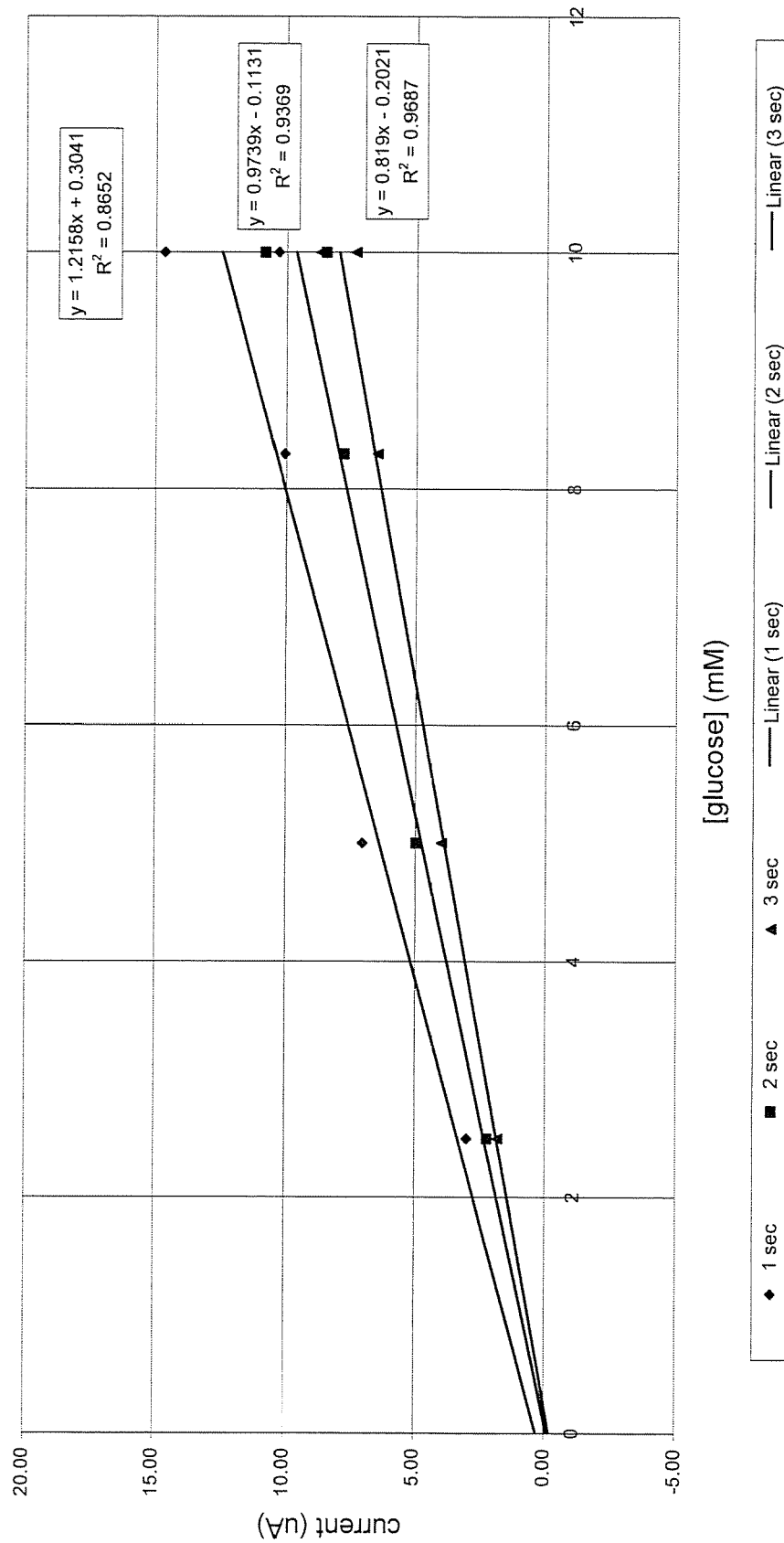
FIG. 11 is a graph showing the electrode calibrations at 1, 2, and 3 second assay times with $[Ni(PQ)_3]Cl_2$ and glucose dehydrogenase with pyrroloquinolinequinone (GDH/PQQ).

FIG. 9 shows the electrode calibrations at 1, 2, and 3 second assay times with [Ni(PQ)$_3$]Cl$_2$ and D-3-hydroxybutyrate dehydrogenase (HBDH). FIG. 10 shows the electrode calibrations at 1, 2, and 3 second assay times with [Ni(PQ)$_3$]Cl$_2$ and glucose dehydrogenase with nicotinamide adenine dinucleotide (GDH/NAD). FIG. 11 shows the electrode calibrations at 1, 2, and 3 second assay times with [Ni(PQ)$_3$]Cl$_2$ and glucose dehydrogenase with pyrroloquinolinequinone (GDH/PQQ). Therefore, as provided in the figures the reagent composition of the present invention is suitable for use with a variety of different enzymes for detection of an analyte.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A method for determining the concentration of an analyte in a sample of biological fluid, the method comprising the steps of:
   inserting a biosensor into an analyte monitor, the biosensor comprising:
      an electrode support having at least one electrode thereon; and
      a reagent composition disposed on the at least one electrode, the reagent composition comprising:
         an enzyme;
         a mediator, wherein the mediator is 1,10-phenanthroline-5,6-dione or a derivative thereof;
         a magnesium ion; and
         a counter anion;
   applying the biological fluid to the biosensor;
   applying a voltage at the electrode;
   measuring the current at the electrode; and
   correlating the current measured to the concentration of the analyte.

2. The method of claim 1, wherein the magnesium ion is complexed with the mediator.

3. The method of claim 1, wherein the counter anion is a halide, a nitrate, a nitrite, a sulfate, a carbonate, a phosphate, a thiocyanate, an acetate, a formate, a citrate, a succinate, an oxalate, a tartrate, a benzoate, or an alkyl or aromatic sulfonate.

4. The method of claim 3, wherein the halide is chloride, bromide, fluoride, or iodide.

5. The method of claim 1, wherein the counter anion is a tungstate, a molybdate, a ferricyanide, a nitroprusside, a tetraphenylborate, or an anionic surfactant.

6. The method of claim 1, wherein the enzyme is selected from the group consisting of glucose oxidase, glucose dehydrogenase and 3-hydroxybutyrate dehydrogenase.

7. The method of claim 1, wherein the enzyme is an NAD(P)$^+$-dependent dehydrogenase.

8. The method of claim 1, further comprising a covering layer defining an enclosed space over the at least one electrode, the covering layer having an aperture for receiving a sample into the enclosed space.

9. The method of claim 8, further comprising a least one layer of mesh interposed in the enclosed space between the covering layer and the at least one electrode.

10. The method of claim 1, wherein the biosensor comprises a working electrode, a reference electrode and a counter electrode, wherein the counter electrode is positioned relative to the working electrode and the reference electrode such that a liquid sample will contact the working electrode and the reference electrode prior to contacting the counter electrode.

11. The method of claim 1, wherein at least one electrode comprises carbon, palladium, gold, platinum, or iridium.

12. A biosensor comprising:
an electrode support;
a working electrode disposed on the electrode support;
a reference electrode disposed on the electrode support; and
a reagent composition deposited over the working electrode and the reference electrode, wherein the reagent composition comprises an enzyme, a mediator, a magnesium ion, and a counter anion, wherein the mediator is 1,10-phenanthroline-5,6-dione or a derivative thereof.

13. The biosensor of claim 12, wherein the magnesium ion is complexed with the mediator.

14. The biosensor of claim 12, wherein the counter anion is a halide, a nitrate, a nitrite, a sulfate, a carbonate, a phosphate, a thiocyanate, an acetate, a formate, a citrate, a succinate, an oxalate, a tartrate, a benzoate, or an alkyl or aromatic sulfonate.

15. The biosensor of claim 14, wherein the halide is chloride, bromide, fluoride, or iodide.

16. The biosensor of claim 12, wherein the counter anion is a tungstate, a molybdate, a ferricyanide, a nitroprusside, a tetraphenylborate, or an anionic surfactant.

17. The biosensor of claim 12, wherein the enzyme is selected from the group consisting of glucose oxidase, glucose dehydrogenase and 3-hydroxybutyrate dehydrogenase.

18. The biosensor of claim 12, wherein the enzyme is an NAD(P)$^+$-dependent dehydrogenase.

19. The biosensor of claim 12, further comprising a covering layer defining an enclosed space over the working electrode and reference electrode, the covering layer having an aperture for receiving a sample into the enclosed space.

20. The biosensor of claim 12, further comprising at least one layer of mesh interposed in the enclosed space between the covering layer and the working electrode and reference electrode.

21. The biosensor of claim 12, further comprising a counter electrode, wherein the counter electrode is positioned relative to the working electrode and the reference electrode such that a liquid sample will contact the working electrode and the reference electrode prior to contacting the counter electrode.

22. The biosensor of claim 12, wherein at least one electrode comprises carbon, palladium, gold, platinum, or iridium.

23. A reagent composition, comprising:
a mediator, wherein the mediator is 1,10-phenanthroline-5,6-dione or a derivative thereof;
at least one magnesium ion; and
at least one counter anion.

24. The reagent composition of claim 23, wherein the magnesium ion is complexed with the mediator.

25. The reagent composition of claim 23, wherein the counter anion is a halide, a nitrate, a nitrite, a sulfate, a carbonate, a phosphate, a thiocyanate, an acetate, a formate, a citrate, a succinate, an oxalate, a tartrate, a benzoate, or an alkyl or aromatic sulfonate.

26. The reagent composition of claim 25, wherein the halide is chloride, bromide, fluoride, or iodide.

27. The reagent composition of claim 23, wherein the counter anion is a tungstate, a molybdate, a ferricyanide, a nitroprusside, a tetraphenylborate, or an anionic surfactant.

28. The reagent composition of claim 23, wherein the reagent composition further comprises an enzyme.

29. The reagent composition of claim 28, wherein the enzyme is selected from the group consisting of glucose oxidase, glucose dehydrogenase and 3-hydroxybutyrate dehydrogenase.

30. The reagent composition of claim 28, wherein the enzyme is an NAD(P)$^+$-dependent dehydrogenase.

* * * * *